United States Patent [19]

Chalupa et al.

[11] Patent Number: 5,004,728
[45] Date of Patent: Apr. 2, 1991

[54] METHODS OF INCREASING MILK YIELDS IN RUMINANTS

[75] Inventors: William Chalupa, Malvern; David S. Kronfeld, Coatesville, both of Pa.; Paul L. Schneider, Milwaukee, Wis.; David Sklan, Rehovot, Israel

[73] Assignee: The Trustees of the University of Pennsylvania, Philadelphia, Pa.

[21] Appl. No.: 166,709

[22] Filed: Mar. 11, 1988

[51] Int. Cl.$^5$ ............................................. A61K 37/36
[52] U.S. Cl. ..................................... 514/12; 514/558; 514/560
[58] Field of Search ......................... 514/12, 558, 560

[56] References Cited

U.S. PATENT DOCUMENTS 4,642,317  2/1987  Palmquist ........................... 514/558
4,816,568  3/1989  Hamilton, Jr. ....................... 514/970

FOREIGN PATENT DOCUMENTS 1188221  6/1985  Canada .

OTHER PUBLICATIONS

Keshet, *Nucleic Acids Research,* 9, No. 1, 19-30, (1981).
Schneider, et al., "Bovine Somatotropin and Ruminally Inert Fat in Early Lactation", J. Dairy Sci. 70(Suppl 1): 177, 1987.

*Primary Examiner*—F. T. Moezie
*Attorney, Agent, or Firm*—Woodcock Washburn Kurtz Mackiewicz & Norris

[57] ABSTRACT

Novel methods for increasing milk yields in lactating ruminants are disclosed wherein somatotropin and salts of long chain fatty acids are administered generally coextensive in time to the animals in amounts sufficient to increase the production of milk.

26 Claims, No Drawings

METHODS OF INCREASING MILK YIELDS IN RUMINANTS

Optimizing production of human foods results in lower production costs and ultimately lower costs to consumers. Increased production of milk has long been a goal of farmers and various methods such as food supplements, breeding programs, drugs, hormones, and combinations of feeds have been tried in efforts to increase milk production.

One key to optimizing production of human food is understanding the regulation of nutrient utilization for productive functions. Wide variations in growth rates, composition of gain, and milk yields between animals clearly show that differences in nutrient utilization exist in food-producing animals. Much of the variation may be explained by difference in hormonal status.

Somatotropin is a naturally occurring hormone produced in the pituitary gland of animals, including humans and bovines. This hormone promotes the general growth of the organism. It promotes skeletal growth, protein anabolism, fat metabolism, carbohydrate metabolism and water and salt metabolism.

It is known that somatotropin increases the secretion of milk in lactating cows. Early research on the effects of somatotropin demonstrated that administration of a preparation rich in somatotropin stimulated milk secretion. Another study showed that somatotropin injection for several weeks improved milk production at peak lactation by 50% in grazing cows. Subsequent studies with purer preparations failed to show such a pronounced improvement, however, so that earlier preparations may have contained active and synergistic impurities.

More recent research indicates that bovine somatotropin (BST), whether derived from the pituitary or produced by recombinant DNA techniques increases milk yield and efficiency of milk production in high producing cows, in all stages of lactation and for extended periods of time. Daily injections of 13.5, 27.0 and 40.8 mg/d of bovine somatotropin increased fat-corrected milk (FCM) from 23 to 41% over controls. These cows were in negative energy balance until about 10 weeks into the trial. In another study, cows injected with 50 IU bovine somatotropin daily during weeks 3 and 4 postpartum produced 4.7 kg/d milk over controls. Daily output of energy in milk was increased by 2.54 Mcal.

Somatotropin is also known to increase blood flow to the mammary gland and increase uptake of triglycerides by the mammary gland. Blood flow to the mammary gland was increased by 32% and mammary uptake of triglycerides was increased by 28% with somatotropin. Milk lipid concentration is also increased by administration of somatotropin to lactating cows. Milk lipid concentration increased 40% and percent milk fat increased 25% with cows averaging −13.7 Mcal/d energy balance in response to bovine somatotropin compared to controls. Milk produced by the cows contained fewer short and medium chain fatty acids and more long chain fatty acids, especially 18.1 (oleic acid).

Diets normally fed to maximize milk production contain large amounts of grain, which is highly glucogenic. Lipogenic nutrients must also be supplied in the diet or long chain fatty acids (LCFA) may be mobilized from body fat increasing hepatic ketogenesis and the risk of spontaneous ketosis. High yielding dairy cows mobilize over 50 kg of body fat to help meet energy demands during early lactation. When LCFA are supplied in the diet, the risk of ketosis is decreased.

Dietary fat (mostly LCFA) fed to lactating dairy cows increases the energy density of the diet and increases milk yield and milk fat. Long chain fatty acids and 2-carbon acetate provide the majority of the energy for milk synthesis and the oxidative needs of the mammary gland. Direct transfer of LCFA from the diet to milk is more efficient than de novo synthesis from carbohydrates or VFA and is at the expense of short and medium chain fatty acids. Dietary fat has also been shown to decrease plasma insulin concentrations and increase growth hormone/insulin ratio in early lactaton.

It has been found that when the proportion of fat in the diet of cattle exceeds about 2% of the total solids, the feed has toxic effects upon the microorganisms in the rumen of the cattle. It appears that fat reduces the growth rate or even kills certain microorganisms which digest fiber in the cow's rumen, thereby lowering fat digestibility. This deleterious effect on the cow's rumen is particularly noticeable with unsaturated fats. Although the decreased fiber digestion in the rumen is partially compensated for by greater fiber digestion in the lower parts of the alimentary canal, such later fiber digestion produces a blend of different acids that which is produced by the digestion in the rumen and the different blend of fatty acids is less suited to the cow's metabolism.

Due to adverse effects of fat on ruminal fermentation, supplementation of unprotected fat has been limited to about 2% of the diet. In order to reduce these adverse effects and increase the amount of supplementary long chain fatty acids which could be fed to cows, studies with various salts of long chain fatty acids have been conducted. In vitro studies with calcium salts of palm oil indicated that they are inert in the rumen, do not interfere with ruminal fermentation and increase milk yield and milk fat. These salts can thus be fed at higher amounts. Palm oil is largely made up of LCFA (56% - 16:0, 4% - 18:0, 33% - 18:1 and 6.0% - 18:2). U.S. Pat. No. 4,642,317, issued 2/10/87 to Palmquist discloses a method of feeding lactating cows calcium salts of long chain fatty acids from natural sources, particularly tallow because of its low cost. This method allowed supplementation of the diet of lactating cows with calcium salts of long chain fatty acids in the amount of 5% of the dry weight of feed per day or one kilogram of calcium salts of long chain fatty acids per animal per day without ill effects.

There is a need for new methods of increasing milk yields in ruminant animals, especially cows whereby milk production can be increased without adversely affecting the health of the animal. Accordingly, it is an object of this invention to provide methods of increasing the production of milk in lactating ruminants.

SUMMARY OF THE INVENTION

The invention provides methods of improving the production of milk from a lactating ruminant animal. Somatotropin is administered to the animal and generally coextensive in time, the food supply if the animal is supplemented with a long chain fatty acid or long chain fatty acid derivative selected to be substantially inert with respect to the rumination of the animal. Administration of somatotropin and supplementation of the food supply each are in amounts sufficient to effect the improvement in milk production.

The invention further provides methods for improving conversion of dietary foodstuffs into milk in a lactating ruminant animal. Somatotropin is administered to the animal in preferred amounts of from about 5 to about 75 milligrams per day; and a dietary supplement is coadministered to the animal. The dietary supplement preferably comprises a nutritionally acceptable divalent metal salt of a long chain fatty acid, the salt being selected not to interfere with the rumination of the animal and being provided in an amount sufficient to effect the improvement upon the conversion of dietary foodstuffs into milk.

Supplementation of the cow's diet with calcium salts of long chain fatty acids alone does not appreciably increase milk yields. The combination of somatotropin and calcium salts of long chain fatty acids maximizes the cow's response to somatotropin. It is believed that the long chain fatty acids become available to the cow for milk production and allow the cow to secrete more milk in response the somatotropin. Additionally, supplementation of the cow's diet with calcium salts of long chain fatty acids increases the fat content of the milk, thus providing more milk energy per kilogram of milk.

Somatotropin may be administered by any method which does not inactivate the hormone. Injection of somatotropin, mixed with a physiologically acceptable injection vehicle is preferred because it is known that this method of administration does not interfere with the action of somatotropin. Oral administration of somatotropin was ineffective in rats and this may also be the case with cows.

Somatotropin from any species of animal which produces increased milk yields in lactating ruminants is suitable for use in the invention. Natural somatotropin or somatotropin produced by recombinant DNA techniques are suitable for use in the invention. Natural bovine somatotropin and bovine somatotropin produced by recombinant DNA techniques are preferred for use in the invention.

Somatotropin as administered in amounts sufficient to increase production of milk. Amounts of somatotropin between about 5 and 75 milligrams per day are suitable for use in the invention. Administration of between about 40 and 60 milligram per day somatotropin is preferred and administration of about 50 milligrams per day somatotropin is most preferred.

Long chain fatty acids suitable for use in the invention are those having from about 14 to about 26 carbon atoms. Long chain fatty acids having from about 14 to 20 carbon atoms are more preferred for use in the invention and long chain fatty acids having from about 16 to about 18 carbon atoms are the most preferred for use in the invention. The long chain fatty acids may be saturated or partially unsaturated. Long chain fatty acids suitable for use in the invention may be derived from any source, however, the long chain fatty acids are preferably those similar to long chain fatty acids found in natural fats and oils. An example of long chain fatty acids suitable for use in the invention is palm oil. Palm oil comprises a mixture of long chain fatty acids, predominately palmitic acid (16:0, sixteen carbon atoms, saturated), stearic acid (18:0, eighteen carbon atoms, saturated), oleic acid (18:1, eighteen carbon atoms, monounsaturated), and linoleic acid (18:2, eighteen carbon atoms, diunsaturated).

The long chain fatty acid derivative is preferably a long chain fatty acid salt. The salt of the long chain fatty acid can be any salt which does not interfere with the rumination of the animal. The salt of the long chain fatty acid should be substantially inert in the rumen of the animal. Alkaline earth salts which are insoluble in the rumen are most suitable for use in the invention. Calcium salts of long chain fatty acids are preferred.

Free long chain fatty acids may be fed to the lactating ruminant in amounts up to 2% of the animal's diet. However, salt of the long chain fatty acid may be fed to the lactating ruminant in accordance with the invention in amounts from about 0.3 kilograms per day to about 1.0 kilograms per day. Preferred quantities of the salt of long chain fatty acids are about 0.45 kilograms per day to about 0.77 kilograms per day.

The long chain fatty acids or salt of long chain fatty acids may be administered to the animal in any convenient manner, preferably beginning from about 25 to about 120 days post partum. For example, the long chain fatty acid or salt of long chain fatty acid may be mixed with the animal's feed as a food supplement.

The practice of the methods of the invention may begin at any time after parturition. It is believed that cows will respond to the methods of the invention at any time during the lactation cycle. Preferred times for beginning practice of the methods of the invention are between about 25 days and 120 days post partum.

Because milk from cows is consumed by humans, it is critical that the milk be safe for humans. It is believed that bovine somatotropin should not affect humans of enzymatic degradation in the digestive system and lack of activity in humans. Action of bovine somatotropin in humans has been studied in connection with growth studies. In attempts to increase growth rate of hypopituitary dwarfs, several researchers evaluated activity in man of somatotropin derived from bovine pituitaries. Somatotropin at doses of 10 to 160 mg/day did not affect growth of hypopituitary dwarfs and did not change balances of nitrogen calcium and phosphorus in normal subjects. There are structural, biological and immunological differences between human and bovine somatotropin and it does not appear to have effects in humans. Only somatotropin from primates has been found to be active in humans.

Further, low levels of somatotropin in milk are believed to be degraded by proteolytic enzymes in the digestive tract. Both human and bovine somatotropins are inactivated by treatment with the digestive enzymes pepsin, trypsin and chymotrypsin. Recombinantly derived bovine somatotropin has been found to be biologically active in rats when injected but oral administration of up to 10 mg/kg body weight was ineffective.

Milk from cows not treated with bovine somatotropin often contains low levels of somatotropin. One study has shown that daily injection of cows with bovine somatotropin did not increase concentrations of somatotropin in milk serum above that measured in non-treated cows (i.e. 0 to 3 parts per billion). In another study, cows injected with up to 50 mg/day bovine somatotropin did not have detectable levels of somatotropin in milk (validated sensitivity of RIA method was 22 parts per billion), while in another study milk from control and treated cows (40 mg/day bovine somatotropin) contained less than 2.5 parts per billion.

Additionally, pasteurization and other manufacturing processes are believed to inactivate the low levels of somatotropin usually found in milk. Activity of somatotropin is lost by immersion in boiling water at pH 4.0, 7.5 and 8.9. Activity of recombinantly derived bovine somatotropin was lost after pasteurization.

The following examples explain and illustrate the preferred embodiments of the present invention. One of ordinary skill in the art will readily recognize that numerous substitutions or alterations from the examples set forth may be made without departing from the spirit of the present invention, which is defined more particularly in the appended claims.

EXAMPLE 1

| BST, mg/d | 0 | | 50 | |
|---|---|---|---|---|
| CA-LCFA, kg/d | 0 | .77 | 0 | .77 |
| Milk, kg/d | $36.0^a$ | $35.7^a$ | $37.6^a$ | $40.3^b$ |
| 3.5% FCM, kg/d | $33.8^a$ | $33.5^a$ | $36.9^{ab}$ | $40.3^b$ |
| 3.5% FCM/Feed | $1.49^a$ | $1.52^a$ | $1.73^b$ | $1.95^c$ |
| Milk energy, Mcal/d | $23.2^{ab}$ | $23.0^a$ | $25.1^{bc}$ | $27.2^c$ |

$^{abc}p = .05$

Sixteen cows were randomly assigned to either a 0 or 50 milligrams per day somatotropin group four weeks postpartum. Within each group cows received either 0 or 0.77 kilograms per day calcium salts of long chain fatty acids (Megalac, Church and Dwight Co., Inc.) in a single reversal with 5 week periods. Cows receiving 50 milligrams per day bovine somatotropin (American Cyanamid) produced more milk and 4% fat-corrected milk (FCM), had higher gross efficiency and greater energy output into milk. There was no response to calcium salts of long chain fatty acids when no bovine somatotropin was administered. Response to calcium salts of long chain fatty acids with 50 milligrams per day of somatotropin was greater than with 50 milligrams per day bovine somatotropin alone. Ruminally inert calcium salts of long chain fatty acids tended to help cows receiving somatotropin in early lactation achieve increased production potential.

EXAMPLE 2

Cows in early lactation were supplemented with 0 or 1 pound (0.45 kg) calcium salts of palm oil (Megalac, Church and Dwight Co., Inc.) and supplemented daily with 0 or 50 milligrams per day bovine somatotropin (American Cyanamid). In the absence of supplemental fat, bovine somatotropin increased production of 3.5% FCM 6.8 pounds per day over controls receiving no bovine somatotropin. With supplemental fat, bovine somatotropin increased production of 3.5% FCM 14.3 pounds per day. Thus, rumen bypass fat was needed to maximize responses to supplemental bovine somatotropin.

EXAMPLE 3

Cows in early lactation were supplemented with 0 or 0.45 kilograms per day calcium salts of palm oil fatty acids (Megalac, Church and Dwight Co., Inc.) and injected daily with 0 or 50 mg bovine somatotropin (American Cyanamid). In the absence of supplemental fat, injection of bovine somatotropin increased production of 3.5% FCM 3.9 kilograms per day. With supplemental fat, injection of bovine somatotropin increased production of 3.5% FCM 7.3 kilograms per day. Supplemental fat did not increase production of milk in the absence of bovine somatotropin but when cows were injected with bovine somatotropin, fat supplementation increased 3.5% FMC 3.1 kilograms per day.

What is claimed is:

1. A method for improving the production of milk from a lactating ruminant animal comprising:
   administering to the animal somatotropin in an amount sufficient to increase production of milk; and
   generally coextensive in time within said administration, supplementing the food supply for the animal with a long chain fatty acid or long chain fatty acid salt selected to be substantially inert with respect to the rumination of the animal; said administration and said supplementation each being in amounts sufficient to effect the improvement in production.

2. The method of claim 1 wherein the animal is a cow and the somatotropin is bovine somatotropin.

3. The method of claim 2 wherein the long chain fatty acid is a fatty acid having from about 14 to about 26 carbon atoms.

4. The method of claim 3 wherein said fatty acid has about 14 to 20 carbon atoms.

5. The method of claim 3 wherein said fatty acid is palmitic acid.

6. The method of claim 2 wherein the salt is an alkaline earth salt.

7. The method of claim 6 wherein the fatty acid derivative is a calcium salt of the fatty acid.

8. The method of claim 7 wherein the fatty acid derivative is calcium palmitate.

9. The method of claim 2 wherein said somatotropin is administered in an amount of between about 5 and about 75 milligrams per day.

10. The method of claim 9 wherein the somatotropin is administered in an amount between about 40 and 60 milligrams per day.

11. The method of claim 10 wherein the somatotropin is administered in an amount of about 50 milligrams per day.

12. The method of claim 2 wherein said long chain fatty acid derivative is provided in the amount of from about 0.30 kilograms per day to about 1.0 kilogram per day.

13. The method of claim 12 wherein said long chain fatty acid derivative is provided in the amount of from about 0.45 kilograms per day to about 0.77 kilograms per day.

14. The method of claim 2 wherein said administration and supplementation commence from about 25 to 120 days post partum.

15. A method of improving conversion of dietary foodstuffs into milk in a lactating ruminant animal comprising;
   administering to the animal an amount of somatotropin from about 5 to about 75 milligrams per day; and coadministering to the animal a dietary supplement comprising a nutritionally acceptable alkaline earth salt of a long chain fatty acid, said salt being provided in an amount sufficient to effect said improvement of conversion of dietary foodstuffs into milk.

16. The method of claim 15 wherein the animal is a cow and the somatotropin is bovine somatotropin.

17. The method of claim 16 wherein the long chain fatty acid is a fatty acid having from about 14 to about 26 carbon atoms.

18. The method of claim 17 wherein said fatty acid has about 14 to 20 carbon atoms.

19. The method of claim 18 wherein said fatty acid is palmitic acid.

20. The method of claim 16 wherein the salt is a calcium salt of the fatty acid.

21. The method of claim 20 wherein the salt is calcium palmitate.

22. The method of claim 16 wherein the somatotropin is administered in an amount between about 40 and 60 milligrams per day.

23. The method of claim 22 wherein the somatotropin is administered in an amount of about 50 milligrams per day.

24. The method of claim 16 wherein said long chain fatty acid derivative is provided in the amount of from about 0.30 kilograms per day to about 1.0 kilogram per day.

25. The method of claim 24 wherein said long chain fatty acid derivative is provided in the amount of from about 0.45 kilograms per day to about 0.77 kilograms per day.

26. The method of claim 16 wherein said administration commences from about 25 days to 120 days post partum.

* * * * *